US008334702B2

(12) United States Patent
Agache et al.

(10) Patent No.: US 8,334,702 B2
(45) Date of Patent: Dec. 18, 2012

(54) MICRODEVICE FOR THE IN SITU DETECTION OF PARTICLES OF INTEREST IN A FLUID MEDIUM AND OPERATING METHOD

(75) Inventors: Vincent Agache, St Martin le Vinoux (FR); Guillaume Delapierre, Vif (FR)

(73) Assignee: Commissariat a l'Energie et aux Energies Alternatives, Paris (FR)

( * ) Notice: Subject to any disclaimer, the term of this patent is extended or adjusted under 35 U.S.C. 154(b) by 238 days.

(21) Appl. No.: 12/731,963

(22) Filed: Mar. 25, 2010

(65) Prior Publication Data

US 2010/0244855 A1    Sep. 30, 2010

(30) Foreign Application Priority Data

Mar. 26, 2009  (FR) ..................................... 09 01428

(51) Int. Cl.
   *G01R 27/32* (2006.01)
   *G01N 11/00* (2006.01)
(52) U.S. Cl. ..................... 324/634; 324/633; 73/53.01
(58) Field of Classification Search .................. None
   See application file for complete search history.

(56) References Cited

U.S. PATENT DOCUMENTS

| | | | | |
|---|---|---|---|---|
| 6,722,200 | B2* | 4/2004 | Roukes et al. | 73/580 |
| 2003/0033876 | A1 | 2/2003 | Roukes et al. | |
| 2005/0070802 | A1* | 3/2005 | Peters et al. | 600/459 |
| 2008/0009002 | A1* | 1/2008 | Gruner et al. | 435/6 |
| 2010/0087013 | A1* | 4/2010 | Lieber et al. | 436/525 |

FOREIGN PATENT DOCUMENTS

| | | |
|---|---|---|
| WO | WO 2008/035273 | 3/2008 |
| WO | WO 2008/070058 | 6/2008 |

OTHER PUBLICATIONS

Ollier et al., "Lateral MOSFET transistor with movable gate for NEMS devices compatible with "IN-IC" integration," *Nano/Micro Engineered and Molecular Systems*, Jan. 6, 2008, pp. 764-769.
Ernst et al., "Novel Si-Based nanowire devices: Will they serve ultimate MOSFETs scaling or ultimate hybrid integration," *IEEE International Electron Devices Meeting*, Dec. 15, 2008, pp. 1-4.
Search Report for Application No. FR 0901428 dated Oct. 29, 2009.

* cited by examiner

*Primary Examiner* — Vinh Nguyen
(74) *Attorney, Agent, or Firm* — Alston & Bird LLP

(57) ABSTRACT

The invention relates to a detection device of small size, allowing direct in situ detection of particles with no labelling, enabling the particles to be rapidly analysed, and having both a specificity and a sensitivity that are at least equivalent to the existing devices. In one embodiment, the invention provides a device having
a nanowire, intended for interacting with the particles of interest, which is suspended between two anchors that define a source and a drain, the source and the drain are configured to be connected to an AC voltage generator and to a DC voltage generator, respectively, in order to generate a first input signal;
an excitation electrode, placed laterally facing the nanowire and configured to be connected to an AC voltage generator, in order to generate a second input signal; and
a measurement electrode placed opposite the excitation electrode relative to the nanowire and generating a single output signal representative of the particles of interest.

19 Claims, 5 Drawing Sheets

Fig. 12
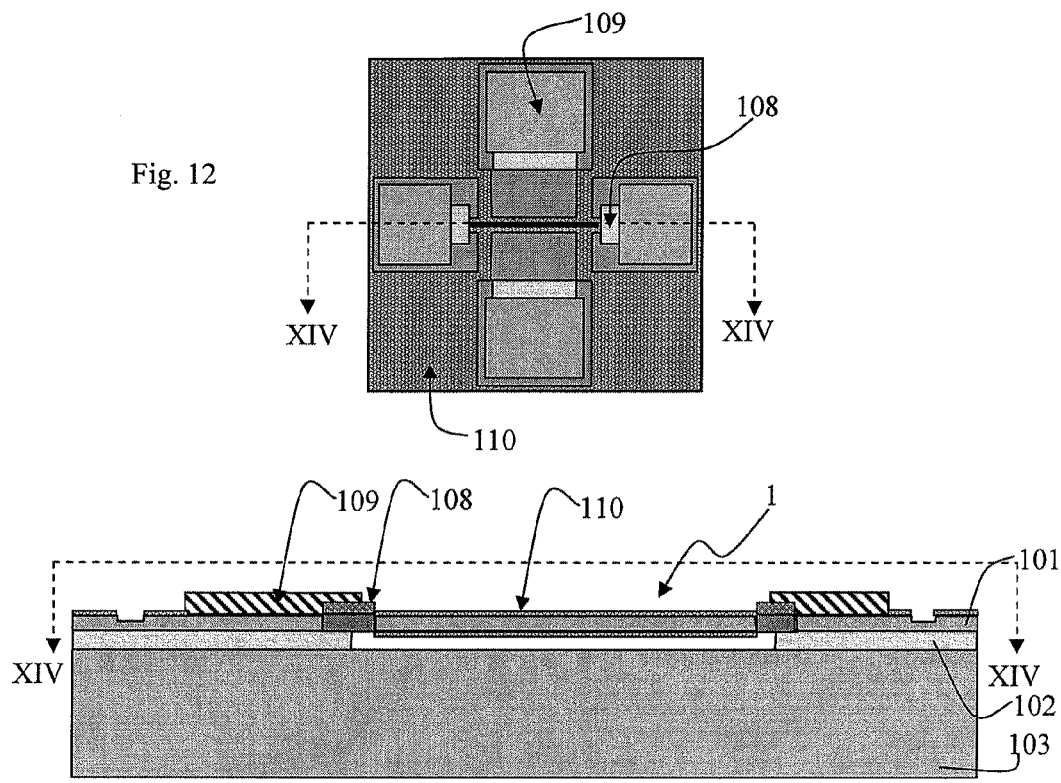
Fig. 13
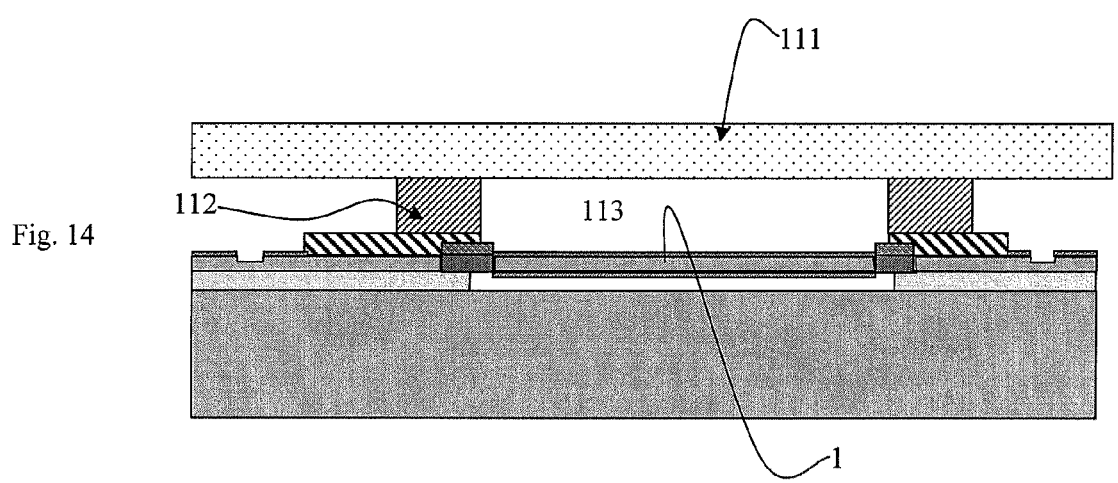
Fig. 14

MICRODEVICE FOR THE IN SITU DETECTION OF PARTICLES OF INTEREST IN A FLUID MEDIUM AND OPERATING METHOD

FIELD OF THE INVENTION

The invention relates to a microdevice for the in situ detection of particles of interest, such as chemical or biological species, in a fluid medium and to an operating method.

BACKGROUND

The detection of chemical particles or biological particles (sequence of nucleotides, proteins, cells, etc.) requires the sensor to have high recognition specificity and optimum sensitivity.

Existing detection means are QCMs (quartz crystal microbalances) with a resolution of 1 ng/cm$^2$ (nanogram per square centimeter), SPR (surface plasmon resonance) with a resolution of 0.05 ng/cm$^2$ or fluorescence.

Other devices have been developed. Some of these use gravimetric analysis, i.e. they detect the shift in resonance frequency when a particle is deposited on the sensor, while others use field-effect detection, i.e. they detect the modification in the semiconductor properties of a CMOS-type sensor when an electrically charged particle is deposited on the sensor (V. Agache et al., "1.1 GHz silicon blade nano-electromechanical resonator featuring 20 nm gap lateral transducers").

Among those using gravimetric analysis, mention may be made of the mass sensor developed by Professor Michael Roukes' team. This sensor is a doubly anchored beam made of silicon carbide (SiC), said beam being excited in an out-of-plane bending mode by magnetostatic transduction with magnetic fields of a few tesla.

This sensor has a resolution of around 7 zg (corresponding to the weight of a 4 kDa molecule, i.e. slightly less than 7 pairs of nucleotides), and has a mass sensitivity of around 0.96 Hz/zg. However, these results were obtained for weighing 30 xenon atoms deposited under a high vacuum ($10^{-10}$ torr) at T=4.2 K on the surface of the oscillators. These experimental conditions make it difficult to use this system for biological purposes, in which field it is necessary instead to actuate the system directly in the medium containing the analytes to be detected.

At the present time, only a few electromechanical sensors employing gravimetric detection operate in a liquid medium.

These sensors have an out-of-plane vibration mode that entails the displacement of a large volume of liquid, thereby degrading the quality factor of the sensors. Furthermore, most often they use a detection means external to the detection device, which proves to be problematic in relation to the noise generated, and to reducing the overall size of the detection device.

Most other proposed solutions do not enable the interaction kinetics to be monitored in real time, i.e. in the medium in which the particles to be detected are located.

This is because they rely instead on determining the added mass on the basis of the frequency measurement, before and after deposition of the particles to be detected (an approach often called the "dip and dry" approach). In this case, labels are often used so as to correlate the measured frequency shift with the amount of mass grafted, by simply counting the nanoparticles on the surface of the resonator (by SEM or AFM).

Another approach consists in incorporating the liquid of interest into the actual sensor. Using this principle, an MIT research team (Scott Manalis et al.) has fabricated a lever provided with an internal fluid stream in which the liquid comprising the particles to be detected circulates. The lever is set into vibration by electrostatic coupling at 220 kHz in a vacuum, while the liquid flows, at a constant flow rate, in the fluid stream.

The drawback of this system lies in the method of detection employed (optical detection using a laser and a photodiode having 4 external quadrants), which contribute to the overall size of the system, and in the complexity of the process for fabricating these devices.

In conclusion, none of the approaches proposed hitherto, using gravimetric detection based on an MEMS/NEMS oscillator, is capable of producing a small portable detection device (i.e. comprising measuring means integrated with the sensor on the same chip) for real-time detection in a liquid medium.

However, there are devices for detecting particles by a field effect. Their use in a liquid medium has been known since the beginning of the '70s.

Many technological developments have enabled nanoscale CMOS sensors, such as silicon nanowires or carbon nanotubes, to be produced.

Based on the same principle of conductance modification by charges, these devices have demonstrated high sensitivity in biological interaction detection applications. The drawback of this kind of device is the fact that the sensor and the molecule to be detected are of comparable size (ranging from a few nanometers to a few tens of nanometers). The addition of one or more molecules on the detector therefore greatly disturbs it. The specificity is provided by the probe molecule grafted onto the surface of the device. This therefore requires expensive high-resolution lithography tools for defining nanoscale sensors.

Thanks to CVD (chemical vapour deposition) growth, it is now possible to detect biological molecule concentrations comparable to those that can be detected by conventional fluorescence methods: a few femtomoles of DNA; a few picograms per milliliter of proteins; or a single viral particle.

These results have also been reproduced on silicon nanowires fabricated by post-photolithography silicon etching processes. Although the dimensions of the wires obtained by these technologies (50 nm to several hundred nm) are not as small as those obtained by CVD growth (10-30 nm), the experimental results of biological interaction measurement are nevertheless very good: detection of 25 femtomoles of DNA has recently been demonstrated.

Very good results have also been achieved on carbon nanotubes or sheets or carbon nanotubes. This technology has the advantage of not requiring expensive technology, but benefitting from the nanoscale properties of objects in solution. For example, DNA concentrations of the order of picomoles have thus been detected.

However, only electrically charged particles may be detected by sensors based on electrical detection by the field effect, so that these sensors are not multi-purpose sensors.

The object of the present invention is to provide an inexpensive, multi-purpose portable detection device, i.e. one with a small size, allowing, using a single nanowire, the in situ detection, directly and with no labels, of the mass and the charge of the biological or chemical particles in the fluid that are fixed onto the nanowire, allowing rapid analysis and having a specificity and a sensitivity that are at least equivalent to the existing devices.

SUMMARY

More particularly, the present invention provides a detection device based on resonant semiconductor nanowires for the specific recognition of unlabelled particles of interest, making it possible to use, in a combined manner or separately, one or other of the aforementioned direct detection methods, namely gravimetric detection and electrical detection.

For this purpose, one subject of the invention is a microdevice for the in situ detection of chemical or biological species in a fluid medium, characterized in that it comprises:

i) a nanowire intended for interacting with the particles of interest, having a length and a width, said nanowire being suspended between two anchors and having a mechanical resonance frequency, the anchors defining a source and a drain, the source being intended to be connected to a first voltage generator generating an AC voltage with a first angular frequency and the drain being intended to be connected to a voltage generator for generating a DC voltage, in order to generate a first input signal;

ii) a first electrode, called excitation electrode, placed laterally and facing the nanowire, said first electrode being intended to be connected to a second voltage generator for generating an AC voltage with a second angular frequency, in order to generate a second input signal; and iii) a second electrode, called measurement electrode, placed laterally and facing the nanowire, on the opposite side from the excitation electrode relative to the nanowire and generating a single output signal representative of the particles of interest.

According to other embodiments:
- the length of the nanowire may be between 0.5 µm and 10 µm, preferably between 2.38 µm and 4.25 µm;
- the width of the nanowire may be between 0.02 µm and 1 µm, preferably between 0.15 µm and 0.27 µm;
- the nanowire may have a length-to-width ratio of greater than 10, preferably between 10 and 100;
- the nanowire may be partly or completely covered with complementary elements for the molecular recognition of particles of interest to be detected;
- the detection microdevice may include a synchronous amplifier;
- the nanowire may have a thickness of between 50 nm and 200 nm; and/or
- the nanowire may be covered with a layer of an insulating dielectric with a permittivity of between 2 and 20.

Another subject of the invention is a method of operating the above device, comprising the following steps:
- the source is supplied with a first AC voltage, called the carrier voltage, having a first angular frequency different from the mechanical resonance frequency of the nanowire;
- the drain is supplied with a DC voltage;
- the excitation electrode is supplied with a second AC voltage, called the control voltage, having a second angular frequency equal to the sum of the first angular frequency and the mechanical resonance frequency of the nanowire;
- at least one particle of interest is deposited on the nanowire; and
- a current output by the measurement electrode is detected.

According to a preferred embodiment, the first AC voltage may be supplied by a synchronous amplifier.

According to a preferred embodiment, the method comprises the detection of a frequency component of the source-drain current.

Thus, the invention makes it possible to combine, on the same nanowire, gravimetric detection with field-effect electrical detection, for estimating the mass and the charge of the biological or chemical particles deposited thereon. This invention has a particular advantage in the case of charged particles (for example biological species), in which both methods may be used for detection with the same nanowire. In the case of neutral particles, only gravimetric detection will be used.

BRIEF DESCRIPTION OF THE DRAWINGS

Other features of the invention will be given in the detailed description below, with reference to the figures that show, respectively:

FIGS. 3 to 14, schematic views of one example of a process for fabricating a microdevice according to the invention starting from an SOI substrate.

DETAILED DESCRIPTION

Figure 1:
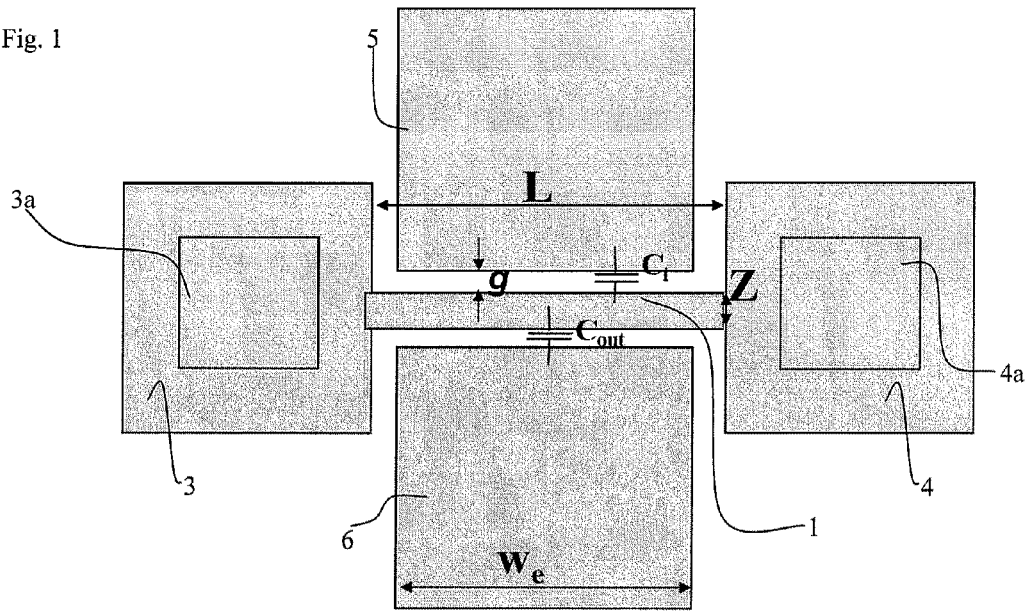
FIG. 1, a schematic top view of a detection microdevice according to the present invention.
Figure 2:
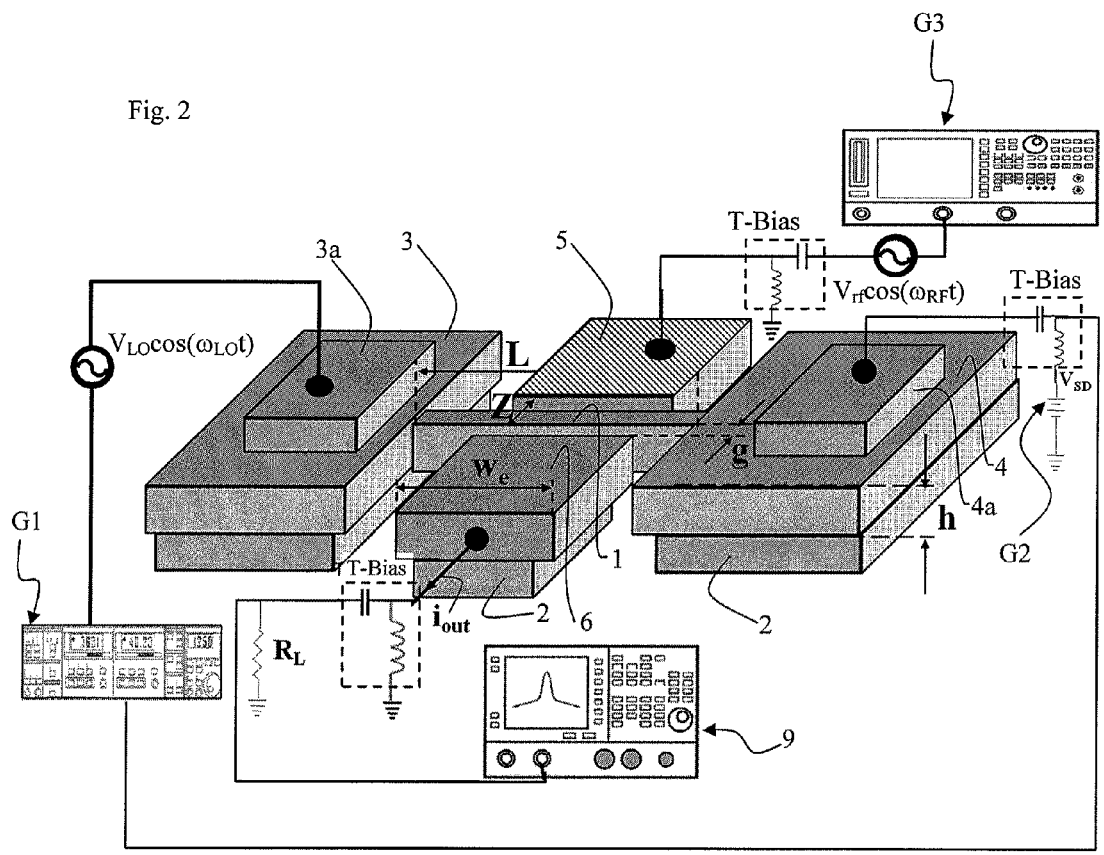
FIG. 2, a schematic perspective view of a detection microdevice according to the present invention electrically connected to electric voltage sources and to an electrical measurement apparatus.

The detection microdevice illustrated in FIGS. 1 and 2 comprises a nanowire 1, made of a semiconductor, suspended above a substrate 2 via two anchors 3, 4 at the ends thereof. This nanowire has a thickness h, a width Z and a length L. Ohmic contact pads 3a, 4a, serving as source and drain zones respectively are placed on the anchors, on either side of the nanowire.

The source is intended to be connected to a first voltage generator G1 for generating an AC voltage $v_{LO}$ with a first angular frequency $\omega_{LO}$. The drain 4a is intended to be connected to a voltage generator G2 for generating a DC voltage $V_{SD}$. These two generators generate a first input signal for electrical detection through a field effect.

In this way, for a given source-drain potential drop, the current flowing through the nanowire is measured, as are, more particularly, its variations induced, through the field effect, by the presence of particles of interest deposited on the surface of the nanowire, when the latter are charged.

Another detection means permitted by this device consists in measuring the change in resonance frequency $\omega_0$ of the nanowire 1 when particles of interest are deposited on the surface of said nanowire 1.

To do this, one or more lateral electrodes 5 are placed laterally, facing the nanowire and separated from the nanowire 1 by a gap g. This (these) electrodes 5 has (have) a total width $W_e$ and enables (enable) the nanowire to be set into resonance, in one of its resonance eigenmodes, by electrostatic coupling. The device thus has a transduction area A such that $A=W_e h$.

The excitation electrode(s) 5 is (are) intended to be connected to a second voltage generator G3 generating an AC voltage $v_{RF}$ with a second angular frequency $\omega_{RF}$. This second generator G3 generates a second input signal for gravimetric detection.

Figure 15:
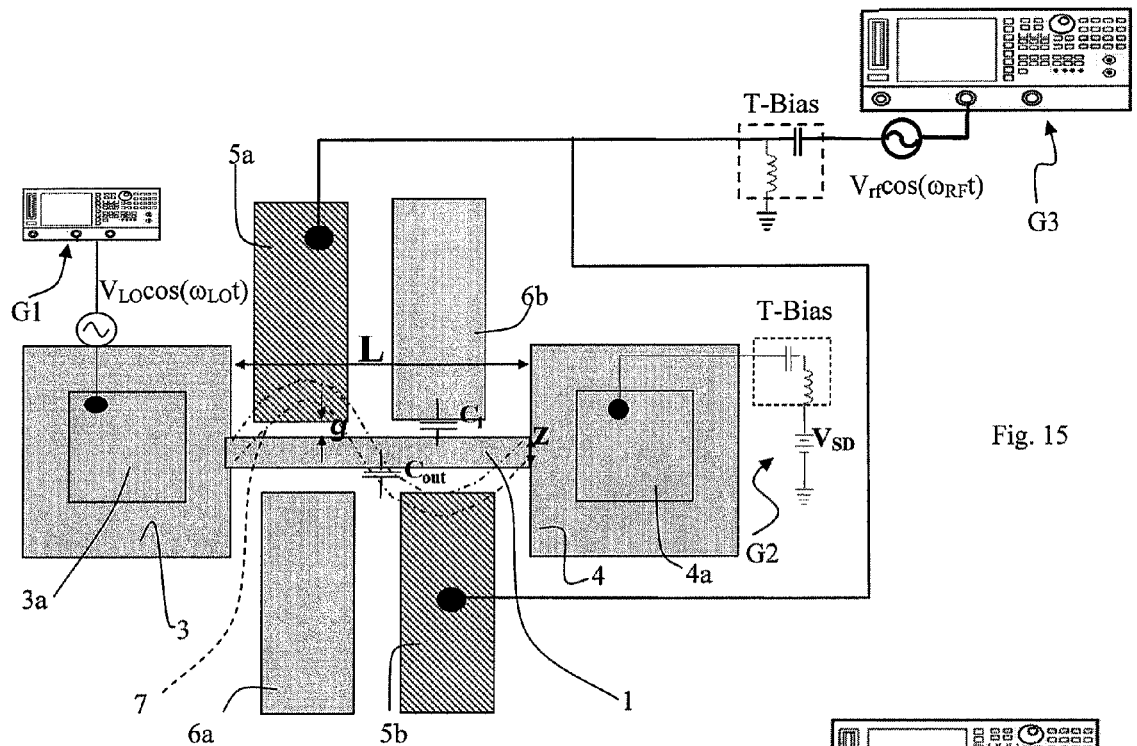
FIGS. 15 and 16, two embodiments of a detection microdevice according to the present invention enabling the nanowire to be set into vibration in its plane, as a harmonic and not in its fundamental mode.
Figure 16:
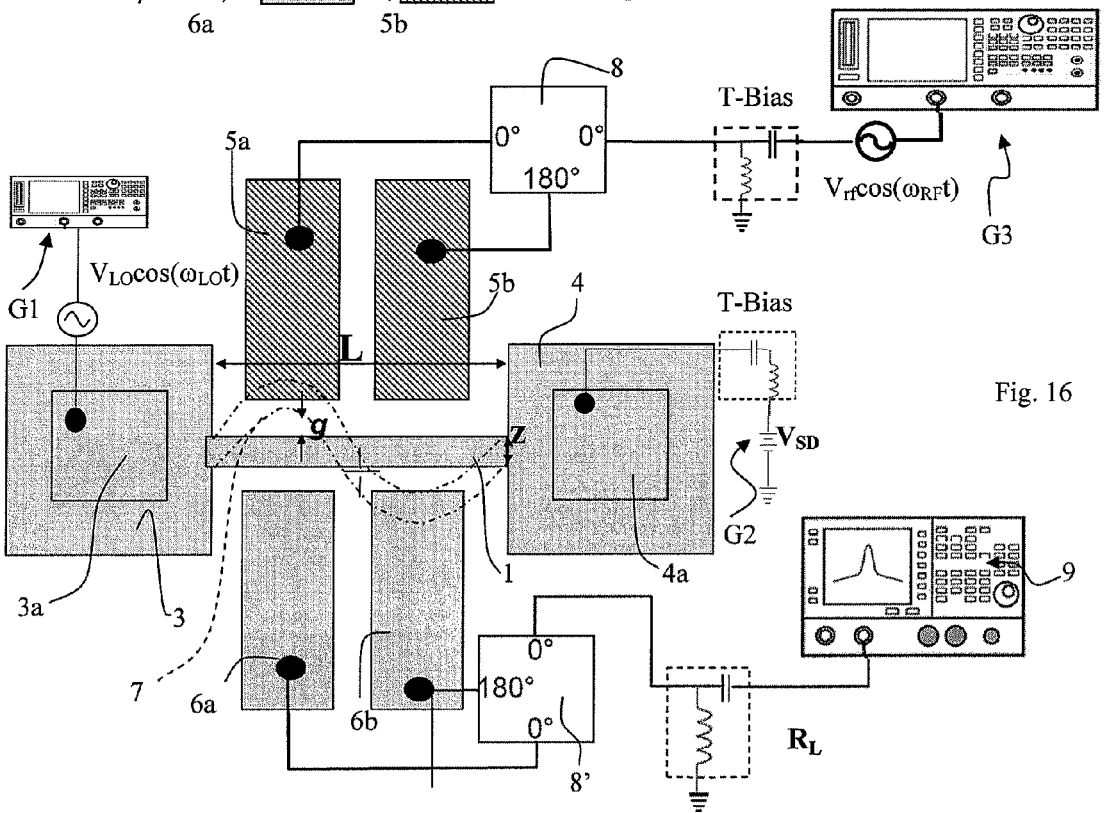

When it is desired to excite the nanowire, not in its fundamental resonance mode but in one of its harmonics, the excitation electrodes 5 may be placed on the same side or on either side of the nanowire, their number and position are adjusted according to the number of vibration antinodes (maximum amplitude) of the harmonic (see FIGS. 15 and 16). For example, to excite the first harmonic it is preferential to integrate two lateral electrodes 5. The same applies to the measurement electrodes 6 for detection by capacitive coupling. It should be pointed out that by exciting the nanowire at one of its harmonic frequencies it is possible to achieve a better detection limit than that obtained at the fundamental resonance mode.

It will be preferable to choose to stress the nanowire so as to obtain in-plane vibrations. Out-of-plane vibrations may also be generated, but with a lower transduction efficiency.

The vibration amplitudes then modulate the capacitance between the nanowire 1 and at least one measurement electrode 6 and give rise to the appearance of what is called a "motional" current that has maxima at the eigenmodes of said nanowire. When several measurement electrodes are used, the output signal is equal to a combination of the signals from these measurement electrodes. This combination may comprise a signal addition or a signal subtraction. When several electrodes measure in-phase vibrations, the combination is an addition. On the other hand, when two electrodes measure vibrations in phase opposition, the respective signals delivered by these two electrodes are subtracted.

Thus, the measurement electrode 6 (or set of electrodes 6) placed laterally facing the nanowire 1, on the opposite side from the excitation electrode 5 (or excitation electrodes) relative to the nanowire 1, generates a single output signal, representative of the particles of interest, on the basis of the first input signal for electrical detection and of the second input signal for gravimetric detection. This signal $I_{out}$ picked up by a spectrum analyser 9 is representative of the mass of particles of interest that have adhered to the surface of the nanowire.

The variations in the current flowing through the nanowire, through the effect of particles of interest being present that have adhered to the surface of the nanowire, enable the total charge of these particles to be measured. By analysing the frequency component, at the first angular frequency $\omega_{LO}$, of the drain current, it is possible to determine the charge of the molecules grafted onto or deposited on the nanowire. A lock-in synchronous amplifier may be used for this detection, for example by measuring the amplitude of this current, called the source-drain current, at the first angular frequency $\omega_{LO}$, this amplitude then depending on the total charge collected on the nanowire.

Thus, it is possible with the same device to determine both the mass and the charge of particles that have adhered to the nanowire.

The output signal detected results from the combination of the currents emanating from two different transduction sources, optimizing the detection sensitivity of the biosensor: on the one hand the motional current, due to the variation in resonance frequency of the nanowire (for example from a capacitive coupling measurement), and, on the other hand, the current resulting from the change in conductance of the nanowire.

The first transduction mechanism is based on detecting the variation in mass and/or mechanical stiffness of the nanowire through the shift in its resonance frequency induced by particles of interest being deposited on its surface.

The second transduction mechanism is based on electrical detection through a field effect, and more particularly on the modification of the electrostatic environment of the semiconductor nanowire by means of a chemical reaction or a biological recognition at its surface, consequently modulating the current flowing within it. This mechanism, with no labelling of the particles of interest, is particularly advantageous as it has a sensitivity of a few picograms per milliliter (pg/ml) on undiluted sera, in particular enabling the specimen preparation steps to be simplified.

This combination of methods—gravimetric detection and electrical detection through a field effect—has many advantages:
- absence of labelling, thereby simplifying the protocols and reducing analysis time and costs;
- very high sensitivity;
- possible integration, since this detection mode does not require a bulky read system and a CMOS architecture may be envisaged.

According to the invention, it is possible, through suitable signal processing, to extract the useful signal from the direct capacitive noise (input and output electrode coupling) while still characterizing, at the same time, the source-drain current which also provides information about the deposition of particles of interest, when said particles are charged.

More particularly, the method according to the invention consists in adapting one of the input signals according to the other input signal, in order to obtain an output signal enabling the information corresponding to each of the detection methods used to be easily exploited. It is thus possible to obtain a first output signal representative of the mass of the particles of interest bonded to the nanowire and also to obtain a second output signal representative of the total charge of these particles of interest, the two output signals being obtained simultaneously using the same nanowire and using a common input signal.

As illustrated in FIG. 2, the detection microdevice according to the invention is preferably operated by supplying the source 3a with a first AC voltage $v_{LO}$, called the carrier voltage, from a first AC voltage generator G1. This voltage has a first angular frequency $\omega_{LO}$ different from the mechanical resonance frequency $\omega_0$ of the nanowire 1 that it is desired to use. This carrier voltage is generated either by a lock-in synchronous amplifier or by a standard signal generator.

The drain 4a is supplied with a DC voltage $V_{SD}$ from a DC generator G2. This signal is superimposed on the carrier of angular frequency $\omega_{LO}$.

The excitation electrode 5 is supplied with a second AC voltage $v_{RF}$, called the control voltage, from a second AC voltage generator G3. The AC voltage $v_{RF}$ has a second angular frequency $\omega_{RF}$ equal to the sum of the first angular frequency $\omega_{LO}$ and the mechanical resonance frequency $\omega_0$ of the nanowire.

Although none of the applied signals has a frequency identical to the mechanical resonance frequency $\omega_0$ of the nanowire, it is possible to ensure that the resultant of the forces $F_{mix}$ derived from the capacitive coupling to be at this frequency $\omega_0$ by profiting from the quadratic non-linearities inherent in transduction by capacitive coupling. Thus, the total force $F_i$ resulting from the electrostatic coupling is written as:

$$F_i = \frac{1}{2}(V_{SD} + v_{LO} - v_{RF})^2 \left(\frac{\partial C_i}{\partial x}\right) \qquad \text{Equation 1}$$

in which $C_i$ ($C_i = \epsilon_0 \epsilon_r L h/g$) denotes the transduction capacitance between the nanowire 1 and the electrode 5 to which the signal $v_{RF}$ of angular frequency $\omega_{RF} = \omega_0 + \omega_{LO}$, is applied and x is the lateral displacement of the nanowire 1 relative to its neutral axis in the direction of the vibrations, while $\epsilon_0$ and $\epsilon_r$ denote the permittivity of free space and the relative permittivity of the nanowire, respectively.

By decomposing this expression, the following is obtained:

$$F_i = \frac{1}{2}V_{SD}^2\left(\frac{\partial C_i}{\partial x}\right) + \frac{1}{2}v_{LO}^2\left(\frac{\partial C_i}{\partial x}\right) + \frac{1}{2}v_{RF}^2\left(\frac{\partial C_i}{\partial x}\right) + V_{SD}v_{LO}\left(\frac{\partial C_i}{\partial x}\right) - V_{SD}v_{RF}\left(\frac{\partial C_i}{\partial x}\right) - v_{LO}v_{RF}\left(\frac{\partial C_i}{\partial x}\right)$$

and the last term of $F_i$ corresponds to the desired resultant of the forces $F_{mix}$, namely:

$$F_{mix} = -v_{LO}v_{RF}\left(\frac{\partial C_i}{\partial x}\right) = -\frac{1}{2}V_{LO}V_{RF}\left(\frac{\partial C_i}{\partial x}\right)\cos(\omega_{RF} - \omega_{LO})t$$

in which $v_{LO} = V_{LO}\cos(\omega_{LO})t$ and $v_{RF} = V_{RF}\cos(\omega_{RF})t$.

The term $F_{mix}$ resulting from the modulation in the carrier voltage by the control signal $v_{RF}$ then has an angular frequency $\omega_{RF}-\omega_{LO}$ which is adjusted so as to be tuned to the mechanical resonance frequency $\omega_0$ of the nanowire.

Next, the detection microdevice according to the invention is used by depositing at least one particle of interest on the nanowire and detecting the current $I_{out}$ output by the measurement electrode 6.

Thus, the angular frequency $\omega_0$ (i.e. in the resonance eigenmode of the nanowire 1 employed), a motional current having an amplitude given by the following equation is obtained:

$$I_{out} = \omega_0 V_{SD}\left(\frac{\partial C_{out}}{\partial x}\right)\frac{Q}{k_{eff}}F_{mix}, \qquad \text{Equation 2}$$

in which Q denotes the quality factor of the nanowire at the angular frequency $\omega_0 = \omega_{RF}-\omega_{LO}$, and $C_{out}$ denotes the transduction capacitance between the nanowire 1 and the measurement electrode 6.

$C_{out}$ and $k_{eff}$ are the transduction capacitance of the nanowire at the angular frequency $\omega_0$ and the effective stiffness of the nanowire of length L and height h, respectively, where:

$$C_{out} = \varepsilon\varepsilon_0\frac{Lh}{g'}$$

g' being the distance separating the nanowire from the detection electrode (in general g'=g) and:

$$k_{eff} = 32Ew^3h/L^3$$

where E=Young's modulus and w=thickness of the nanowire.

Q corresponds to the quality factor of the nanowire, which may be determined by trials and by modelling. This factor determines the proportion of energy absorbed by the oscillator at a given frequency. It also corresponds to the sharpness of a resonance peak.

Assuming approximation of a harmonic oscillator, the quality factor of such an oscillator is given by:

$$Q = \frac{w_0}{\Delta f_{-3dB}}$$

where $\Delta f_{-3dB}$ represents the mid-height width of the graph of the resonance amplitude as a function of the oscillation frequency of the nanowire.

The advantage of this preferred embodiment lies in the fact that the output signal $I_{out}$ is frequency-shifted relative to the control voltage applied to the excitation electrode 5 and to the carrier voltage applied to the source 3a.

This prevents the direct capacitive coupling being superimposed on the output signal of interest and possibly masks the motional current resulting from the mechanical resonance of the nanowire.

Moreover, the carrier voltage of angular frequency $\omega_{LO}$ is put to advantage, by means of a lock-in amplifier for synchronous detection on the source-drain current (transistor effect), as described above.

Thanks to the use of AC voltages of different defined frequencies, it is thus possible to combine gravimetric detection with electrical detection through a field effect, these being coupled and co-integrated into the same device, without the risk of the various signals mixing. Through the signal processing described above, the current of interest resulting from gravimetric detection is not masked by the direct capacitive current, and a frequency component is detected therefrom, determined as a function of that with which synchronous detection of the source-drain current (transistor effect) is obtained.

Furthermore, the device according to the invention enables measurement integration for both detection modes in the device itself Moreover, the device has a small overall size since a single measurement electrode is sufficient for the two detection methods to be carried out simultaneously.

Surprisingly, the inventors have found that by combining the detection method described above, for implementing both types of detection, with certain nanowire dimensions, a particularly high detection sensitivity of the order of a zeptogram, or even less, is obtained. For example for nanowires 4.25 μm in length and 0.09 μm, 0.15 μm and 0.27 μm in width respectively, a mass resolution, or minimum detectable mass, of the order of a zeptogram or even less is obtained. For a nanowire 0.5 μm in length and 30 nm in width, a mass resolution of $5.51\times10^{-3}$ zg and a transconductance factor (defined by the ratio Z/L) of $60\times10^{-3}$ are obtained. With the latter dimensions, a nanowire with a resolution almost ten times higher than that of a nanowire 2.38 μm in length and 0.15 μm in width is obtained for the same quality factors.

Thus, the detection microdevice according to the invention preferably has a nanowire with a length L between 0.5 μm and 10 μm, preferably between 2.38 μm and 4.25 μm, and a width Z between 0.02 μm and 0.27 μm, preferably between 0.15 μm and 0.27 μm. The active layer of the SOI (silicon on insulator) substrate in which the nanowire is defined (see the fabrication process described later) is considered to be extremely thin, i.e. of the order of a few nanometers to a few tens of nanometers.

According to the invention, the nanowire has a ratio $\alpha_{gm}$ (transductance factor) equal to the width Z divided by the length L of advantageously between $10\times10^{-3}$ and $100\times10^{-3}$, preferably between $15\times10^{-3}$ and $70\times10^{-3}$.

According to the invention, the nanowire has a length/width ratio L/Z of greater than 10, advantageously between 10 and 100.

According to the invention, this ratio is determined by the fabrication constraints. Below a length/width ratio L/Z of 10, the increased stiffness of the nanowires precludes the use of lateral bending modes without substantial mechanical non-linear phenomena. In contrast, when this ratio is greater than 100, the length is too high and, during fabrication of the microdevice according to the invention, a "stiction" phenomenon may occur during release of the nanowire (see the description relating to FIGS. 11).

This ratio will be determined precisely so that, for a given gate voltage $V_g$ (i.e. the charge provided by the particles of interest deposited on the surface of the nanowire 1), the drain current associated with biological detection is a maximum.

The width Z of the nanowire will be greater than 20 nm, but less than 1 μm.

The surface of the nanowire is preferably covered (partly or completely) with complementary elements for recognizing the particles of interest to be detected, so as to promote particle detection and minimize the non-specific adsorption, i.e. the deposition of particles that it is not desired to detect. For example, the recognition elements are chemical or biological molecules, antibodies, nucleic acid probes or imprinted polymers.

The recognition elements are immobilized on semiconducting surfaces of the nanowire which may or may not be covered with a dielectric. The semiconductor may for example be silicon or germanium. The dielectric may for example be a conducting or semiconducting oxide ($SiO_2$) or else a conducting or semiconducting nitride ($Si_3N_4$).

The recognition elements may be grafted onto the surface as a monolayer (with a thickness of a few Angstroms) as a thin film (1 to 10 nm in thickness) made up of a few monolayers or else as a thick film of recognition elements, by themselves or encapsulated in a matrix, for example of the sol-gel or polymer type (with a thickness ranging from a few nm to several hundred nm).

The monolayers enable a given quantity of recognition elements to be precisely controlled, whereas encapsulation in a matrix enables this surface density to be substantially increased, for example for increasing the sensitivity and/or the robustness of the system.

The recognition element may be bonded to the surface covalently or may simply be adsorbed. In general, covalent bonding is preferred as it is more robust. In the case of thick films, simple adsorption may prove to be sufficient.

It should also be noted that the recognition element may be connected directly to the surface or via a chemical linker. The advantage of a linker is that it is easier for attaching the recognition element and/or that the properties (stiffness, conduction, etc.) of the organic/inorganic interface may be modulated. If a linker is used, it must contain a chemical functional group capable of reacting with the recognition element, either covalently or by simple electrostatic, hydrophobic or Van der Waals interaction. To give an example, the covalent bond between the linker and the recognition element may be formed by a link of the following types: C—N, C=N (imine), C—O, amide, ester or triazole (starting from a reaction between an alkyne and an azido group).

Depending on the surface material used, the recognition element or its linker comprises a chemical group suitable for enabling it to be attached to the surface.

By dielectric, such as for example $SiO_2$, $Si_3N_4$ or $TiO_2$, recognition elements or linkers may be used that are provided for example with the following functions:
- silanes ($SiH_3$, $RSiX_3$, $R_2SiX_2$, $R_3SiX$, etc.) in which R is a carbon-containing group and X is a releasable group of the halogeno or alkoxy type;
- phosphates or phosphonates.

On a semiconductor such as silicon, it is possible for example to use functional groups capable of creating Si—C or Si—O bonds. Without being exhaustive, alkene, alkyne, alkoxy, phenol, diazonium and halide groups may be mentioned.

Depending on the desired layer (monolayer, thin film, thick film), a different embodiment is chosen.

Monolayers and thin films are for example produced by dipping the surface into a solvent containing the molecule to be grafted (recognition element or linker) optionally in the presence of one or more catalysts, or else by the Langmuir-Blodgett technique if molecules capable of self-assembly are involved.

Thermal, electrical and/or photochemical activation may also be used. Electrical activation may take place either externally or with the use of source/drain contacts connecting the nanostructure.

Thick polymer films are for example produced by the usual methods employed in sol-gel processes: dip coating, spin coating, laminar flow coating, spraying, etc.

The sensor may operate in a gaseous medium (for example for the detection of toxic or infectious agents in the air) or in an aqueous medium (for the detection of viruses, molecules, immunospecific recognition, etc.). In this design, the active parts in contact with the liquid will be passivated with an insulating layer (of silicon oxide, high-permittivity dielectrics such as $HFO_2$, $Al_2O_3$, etc.) so as to prevent the appearance of leakage currents, for example by electrolysis.

One example of a process for fabricating the device according to the invention is described below with reference to FIGS. 3 to 14.

The starting substrate is preferably an SOI substrate 100 on which the active parts of the device, i.e. the self-supported semiconductor nanowire, the lateral transduction electrodes, for setting the nanowire into vibration and for gravimetric detection by capacitive coupling and the support means, incorporating the source and drain zones for electrical detection through a field effect, are fabricated.

Figure 3:
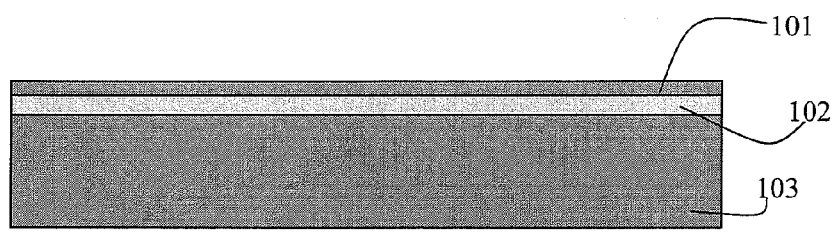

This SOI substrate 100, illustrated in FIG. 3, comprises a p-doped or n-doped single-crystal silicon upper layer 101. This upper layer 101 has a thickness of around 50 to 200 nm. Placed beneath this upper layer is a buried $SiO_2$ layer 102 with a thickness of preferably around 500 nm to 3 microns. Finally, a lower layer 103, made of silicon with a <100> crystallographic direction, lies beneath the buried $SiO_2$ layer.

Figure 4:
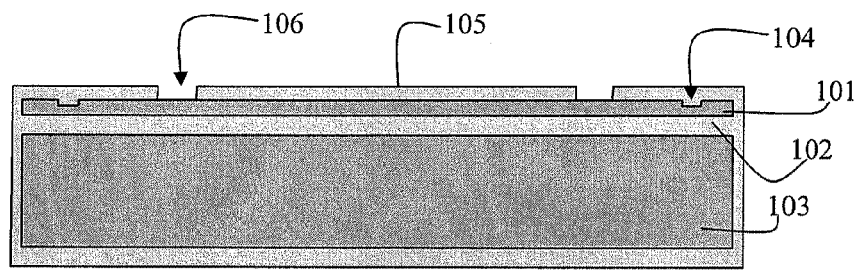

A first step, illustrated in FIG. 4, consists in defining alignment marks 104 by photolithography and dry etching in the upper silicon layer 101. After removal of the protective resist, a thermal oxide is grown in order to form a thermal oxide layer 105. A photolithography operation is then carried out using a protective resist in order to define openings 106 in the thermal oxide layer 105.

Figure 5:
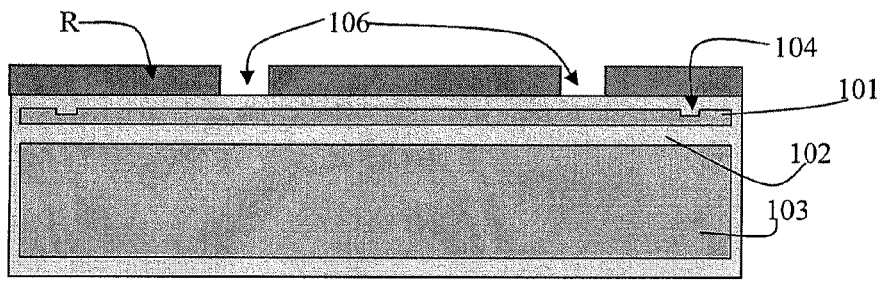

In a preferred embodiment, illustrated in FIG. 5, the protective resist R is retained so as for dopants to be locally implanted through the openings 106. The implantation parameters are adjusted so that the dopants are located on the surface of the single-crystal silicon upper layer. The implanted dopants are chosen to be of the p type if the single-crystal silicon upper layer is initially n-doped, and conversely of the n type if said layer is p-doped. The dopants may be electrically activated at substitutional sites in two different ways:
- the protective resist R is used for transferring the apertures 106 into the thermal oxide layer 105 by RIE (reactive ion etching). The resist is then removed using a suitable chemical solution and the activation annealing is then applied; or alternatively
- the resist is removed just after the implantation step. The activation annealing is then applied and then a photolithography step is again carried out so as to define the same openings (or different openings plumb with the pre-implanted zones) above the oxide that is then etched (by RIE) down to the single-crystal silicon upper layer. The protective resist is then removed.

The second alternative consists in defining relatively wide contact zones and/or contact zones away from the nanowire, with the metal layer 109 that will be subsequently deposited and etched.

Figure 6:
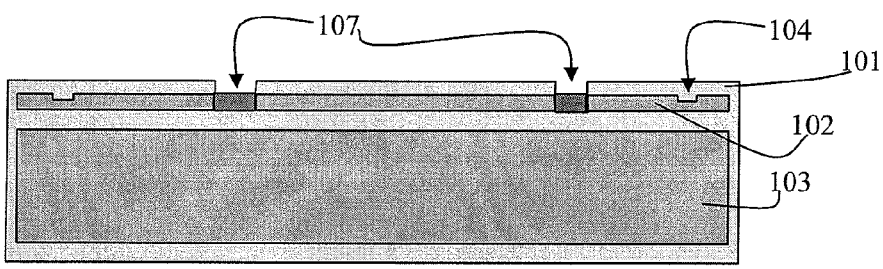

At this stage in the fabrication process, illustrated in FIG. 6, the openings 106 in the thermal oxide are defined on the front surface of the SOI substrate, opening onto p-doped single-crystal silicon "wells" 107 if the SOI upper layer is initially n-doped, and conversely n-doped wells if the upper layer is p-doped. These wells 107 include source and drain zones for the semiconductor nanowire, for the purpose of operating it as a transistor, and optionally the electrical leads on the electromechanical transduction electrodes.

Figure 7:
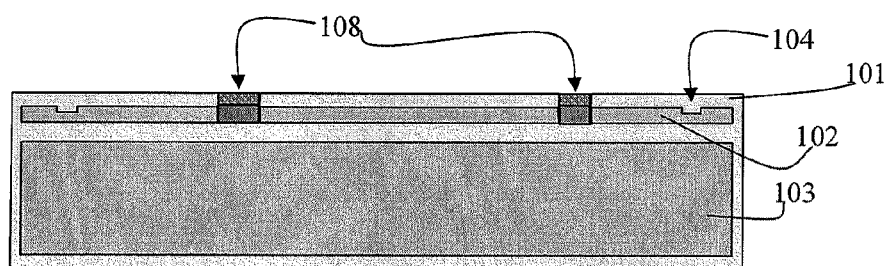

Next, as illustrated in FIG. 7, the front face of the SOI substrate is coated with a metallic layer, after which an annealing operation and selective removal by chemical etching are carried out so that self-aligned ohmic contacts 108 are formed, at the location of the openings 106, on the implanted wells 107, by silicizing titanium, nickel or platinum in an alternative version.

Figure 8:
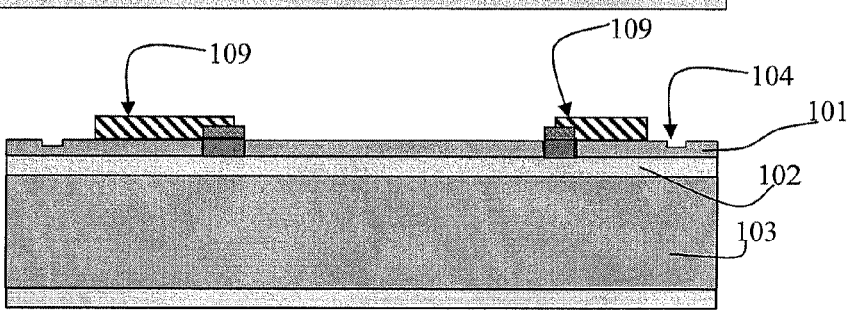

In a preferred embodiment, the thermal oxide layer 105 is then removed using a chemical solution based on hydrofluoric acid, or alternatively using an RIE etching method which is selective with respect to the metal silicide. The front face of the substrate is then covered with an AlSi metallic layer, deposited by low-temperature cathode sputtering (FIG. 8). This metallic layer may also be gold preceded, where appropriate, by a tie layer made of chromium, titanium or nickel.

In an alternative embodiment, the thermal oxide layer 105 is retained before the AlSi is deposited. In this case, the AlSi layer has to be located on the wells and around the latter, since the contact pads 109 are larger in size than the wells.

Figure 9:
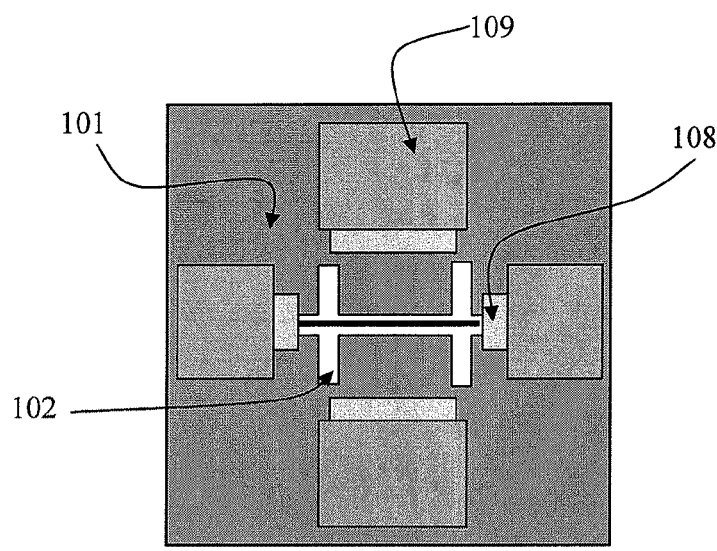
Figure 10:
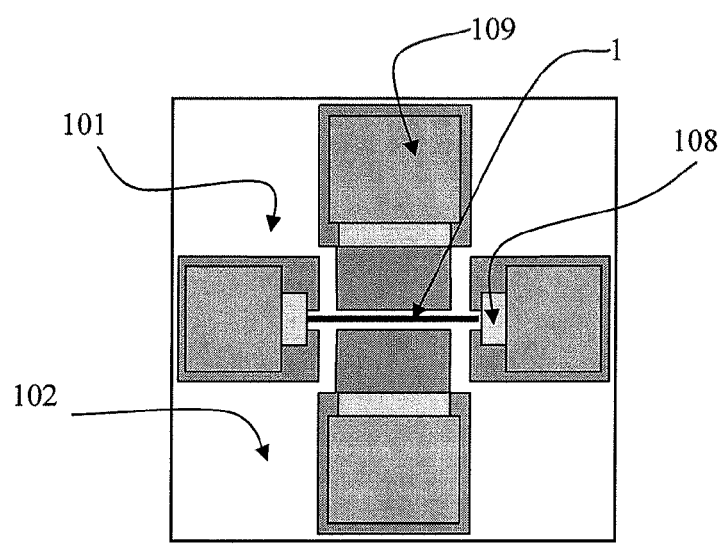

Next, a further photolithography step is carried out that defines a resist mask through which the AlSi layer is removed locally by dry etching. Removing the resist mask results in the formation of AlSi electrical contact pads 109 (FIG. 8) for biasing the future device (source, drain, electromechanical transduction electrodes). These contact pads 109 preferably extend as far as the periphery of the chip, i.e. in the zones away from the future fluid streams or parts in contact with the liquid containing the particles of interest to be detected. FIG. 9 is a top view of the substrate obtained after this fabrication step.

A further photolithography step is then carried out so as to define alignment features for a subsequent electron-beam (e-beam) lithography step.

This e-beam lithography step is used to define the masking feature (positive resist) of the nanowire, together with the adjacent features (lateral electrodes and suspension pads). The features obtained are transferred by dry etching into the silicon oxide upper layer (should the latter have been retained before the AlSi deposition, which is the case for the alternative embodiment mentioned above), and also into the single-crystal silicon upper layer.

The electron resist removal is followed by a further photolithography step, employing a thick photoresist (with a thickness of a few microns), making it possible to define the isolating trenches between the biasing electrodes for the sensor (source, drain and lateral electromechanical transduction electrodes) and, at the same time, to mask the already structured features resulting from the previous e-beam lithography (nanowire and adjacent features). The trenches are obtained by dry etching in the single-crystal silicon upper layer, after which the resist is removed using a dedicated chemical solution followed by an oxygen-based plasma in order to ensure that the polymer residues are completely removed from the gaps, as illustrated, in the top view, in FIG. 10.

Figure 11:
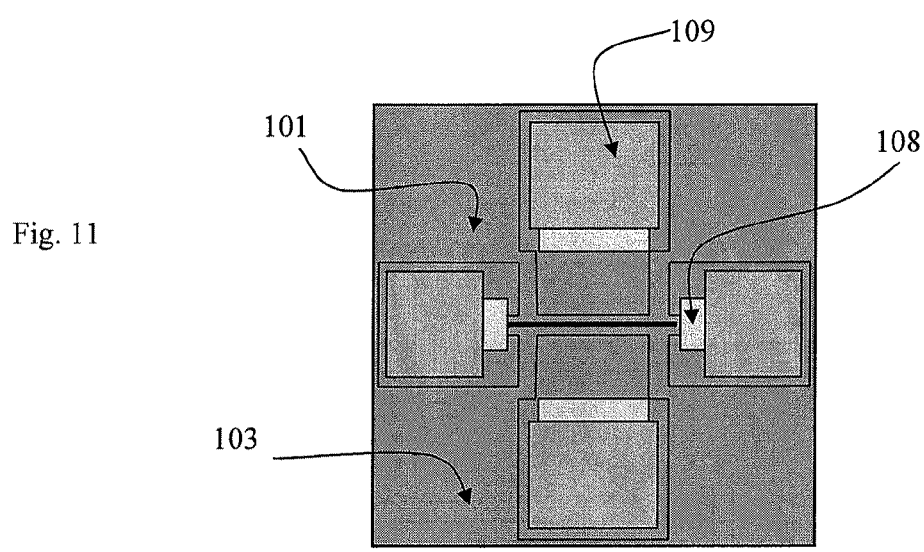

The nanowire is then freed from the substrate by etching the buried oxide 102 in a BOE (buffered hydrochloric acid)-based chemical solution or in a chamber saturated with HF in the vapour phase (FIG. 11). After the oxide beneath the nanowire has been removed by one or other of these chemical etching processes, the specimen is immersed in deionized water followed by isopropanol, before finally being dried in an oven.

As mentioned above, the length/width ratio L/Z is determined by the fabrication constraints. When this ratio is greater than 100, the length of the nanowire is such that there is a risk of a "stiction" phenomenon occurring when freeing the nanowire: while the sacrificial buried oxide layer 102 is being etched, friction or adhesion between the nanowire and the rest of the layer 101 may be observed. In other words, the capillary forces induced by the surface tension of the wet etchant between the nanowire 1 and the rest of the layer 101, during drying of the etchant, cause the nanowire to bond to the rest of the layer 101 or generate friction therebetween. Separating the two surfaces is often complicated due to the fragile nature of the nanowire 1.

After the nanowire has been freed, an ALD (atomic layer deposition) process is used to deposit a layer 110 of a high-k (high-permittivity) oxide, such as an oxide of the $Al_2O_3$ or $HFO_2$ type, or more generally an insulating dielectric deposited conformally, that is to say one in which the thickness is uniform around the wire. It is advantageous to use a high-permittivity oxide deposited by the ALD process since the transduction efficiency between the electrodes 5, 6 and the nanowire 1 is greater the higher the capacitance of the oxide. Preferably, the permittivity will be between 2 and 20.

In a preferred method of implementation, a silicon oxide is then deposited by low-temperature CVD. The high-k oxide/silicon oxide combination is denoted in FIGS. 12 and 13 by the reference 110.

A photosensitive film lamination step followed by photolithography makes it possible to define apertures above the AlSi electrical contact pads (covered at this stage with a PECVD (plasma-enhanced CVD) high-k insulator and $SiO_2$ layer 110). A dry etch enables the insulating layer deposited on the surface to be removed and completely disengages the AlSi through the photosensitive film mask. What is then obtained is the device shown in top view in FIG. 12 and in cross-section in FIG. 13: the entire device is covered with a PECVD high-k insulator and $SiO_2$ layer 110, apart from the AlSi contacts and the ohmic contacts 108.

Finally, in a preferred embodiment shown in FIG. 14, aligned with and bonded onto the front face of the SOI substrate thus structured is an optionally pre-structured cover 111 made of glass or Pyrex® (a transparent cover for observation). This assembly is produced by an adhesive screen-printing process using a biocompatible polymer 112. This polymer undergoes a photolithographic operation so as to contain the channels 113 for circulation of the fluid.

In order to excite the nanowire in one of its harmonics, the excitation electrodes may be placed in series on either side of the nanowire (FIG. 15) or the electrodes are excited with a phase-shifted current (FIG. 16).

In these figures, the number and the position of the electrodes are such that two vibration antinodes (of maximum amplitude) of the harmonic are obtained.

More particularly, the device illustrated in FIG. 15 comprises, on one side of the nanowire 1, an excitation electrode 5a and a measurement electrode 6a. Placed on the other side of the nanowire 1 are a measurement electrode 6b, facing the excitation electrode 5a, and an excitation electrode 5b, facing the measurement electrode 6a.

The electrical connections to the generators G1, G2 and G3 are similar to those illustrated in FIG. 2.

The dotted lines 7 represent the in-plane vibration of the nanowire 1 in its 2nd bending mode.

An alternative arrangement is illustrated in FIG. 16, in which the two excitation electrodes 5a and 5b are placed on the same side of the nanowire 1. Likewise, the two measurement electrodes 6a and 6b are placed on the same side of the nanowire 1, opposite the excitation electrodes 5a and 5b.

The device further includes two phase shifters 8 and 8' connected to the generator G3 and to the spectrum analyser 9, respectively.

The phase shifters enable the electrical currents supplying the excitation electrodes 5a and 5b to be phase-shifted by 180°.

The phase shift between the supply currents makes it possible to obtain an in-plane vibration of the nanowire 1 in its 2nd bending mode.

The phase shifters make it possible to phase shift the currents flowing via the measurement electrodes 6a and 6b so as, by means of the spectrum analyser 9, to recover a single signal.

The invention claim is:

1. Microdevice for an in situ detection of particles of interest in a fluid medium, characterized in that it comprises:
   i) a nanowire configured for interacting with the particles of interest, having a length (L) and a width (Z), said nanowire being suspended between two anchors and having a mechanical resonance frequency ($\omega_0$), the anchors defining a source and a drain, the source being connected to a first voltage generator (generating an AC voltage with a first angular frequency ($\omega_{LO}$) and the drain being connected to a voltage generator for generating a DC voltage ($V_{SD}$), in order to generate a first input signal;
   ii) an excitation electrode, placed laterally and facing the nanowire, said first electrode being connected to a second voltage generator for generating an AC voltage ($v_{RF}$) with a second angular frequency ($\omega_{RF}$), in order to generate a second input signal; and
   iii) a measurement electrode placed laterally and facing the nanowire, on the opposite side from the excitation electrode relative to the nanowire and generating an output signal representative of the particles of interest.

2. Detection microdevice according to claim 1, in which the length (L) of the nanowire is between 0.5 µm and 10 µm.

3. Detection microdevice according to claim 1, in which the length (L) of the nanowire is between between 2.38 µm and 4.25 µm.

4. Detection microdevice according to claim 3 in which the width (Z) of the nanowire is between between 0.15 µm and 0.27 µm.

5. Detection microdevice according to claim 4, in which the nanowire has a length (L) to width (Z) ratio ($\alpha_{gm}$) of greater than 10.

6. Detection microdevice according to claim 5, in which the nanowire has a length (L) to width (Z) ratio ($\alpha_{gm}$) between 10 and 100.

7. Detection microdevice according to claim 3, in which the nanowire has a length (L) to width (Z) ratio ($\alpha_{gm}$) between 10 and 100.

8. Detection microdevice according to claim 1 in which the width (Z) of the nanowire is between 0.02 µm and 0.27 µm.

9. Detection microdevice according to claim 1, in which the nanowire has a length (L) to width (Z) ratio ($\alpha_{gm}$) of greater than 10.

10. Detection microdevice according to claim 1, in which the nanowire has a length (L) to width (Z) ratio ($\alpha_{gm}$) between 10 and 100.

11. Detection microdevice according to claim 1, in which the nanowire is partly or completely covered with complementary elements for the molecular recognition of the particles of interest to be detected, wherein the complimentary elements are selected from the group consisting of chemical or biological molecules, antibodies, nucleic acid probes, and imprinted polymers.

12. Detection microdevice according to claim 1, further comprising a synchronous amplifier.

13. Detection microdevice according to claim 1 in which the nanowire has a thickness of between 50 nm and 200 nm.

14. Detection microdevice according to claim 1 in which the nanowire is covered with a layer of an insulating dielectric having a permittivity of between 2 and 20.

15. Method of operating the microdevice according to claim 1, comprising the following steps:
   supplying the source with a carrier AC voltage ($v_{LO}$), having a first angular frequency ($\omega_{LO}$) different from the mechanical resonance frequency ($\omega_0$) of the nanowire;
   supplying the drain with a DC voltage ($V_{SD}$);
   supplying the excitation electrode with a control AC voltage ($v_{RF}$), having a second angular frequency ($\omega_{RF}$) equal to the sum of the first angular frequency ($\omega_{LO}$) and the mechanical resonance frequency ($\omega_0$) of the nanowire;
   depositing at least one particle of interest on the nanowire; and
   detecting a current ($I_{out}$) output with the measurement electrode.

16. Method according to claim 15, in which the AC voltage ($v_{LO}$) is supplied by a synchronous amplifier.

17. Method according to claim 16, further comprising the step of detecting a frequency component of the source-drain current.

18. Method according to claim 15, further comprising the step of detecting a frequency component of the source-drain current.

19. Method of detecting particles of interest in situ in a fluid medium comprising the steps of:
   providing a device comprising:
   i) a nanowire configured for interacting with the particles of interest, having a length (L) and a width (Z), said nanowire being suspended between two anchors and having a mechanical resonance frequency ($\omega_0$), the anchors defining a source and a drain, the source being connected to a first voltage generator (generating an AC voltage with a first angular frequency ($\omega_{LO}$) and the drain being connected to a voltage generator for generating a DC voltage ($V_{SD}$), in order to generate a first input signal;
   ii) an excitation electrode, placed laterally and facing the nanowire, said first electrode being connected to a second voltage generator for generating an AC voltage ($v_{RF}$) with a second angular frequency ($\omega_{RF}$), in order to generate a second input signal; and
   iii) a measurement electrode placed laterally and facing the nanowire, on the opposite side from the excitation electrode relative to the nanowire and generating an output signal representative of the particles of interest;

supplying the source with a carrier AC voltage ($v_{LO}$), having a first angular frequency ($\omega_{LO}$) different from the mechanical resonance frequency ($\omega_0$) of the nanowire;
supplying the drain with a DC voltage ($V_{SD}$);
supplying the excitation electrode with a control AC voltage ($v_{RF}$), having a second angular frequency ($\omega_{RF}$) equal to the sum of the first angular frequency ($\omega_{LO}$) and the mechanical resonance frequency ($\omega_0$) of the nanowire;

depositing at least one particle of interest on the nanowire; and detecting a current ($I_{out}$) output with the measurement electrode.

* * * * *

UNITED STATES PATENT AND TRADEMARK OFFICE
CERTIFICATE OF CORRECTION

PATENT NO. : 8,334,702 B2
APPLICATION NO. : 12/731963
DATED : December 18, 2012
INVENTOR(S) : Agache et al.

Page 1 of 1

It is certified that error appears in the above-identified patent and that said Letters Patent is hereby corrected as shown below:

Title page,
(73) Assignee: "Commissariat a l'Energie et aux Energies Alternatives" should read
--Commissariat a l'Energie Atomique et aux Energies Alternatives--.

Column 1,
Line 33, "Professor Michael" should read --Professor Michaël--.

Signed and Sealed this
Twelfth Day of March, 2013

Teresa Stanek Rea
*Acting Director of the United States Patent and Trademark Office*